US012274979B2

(12) United States Patent
Hepperle et al.

(10) Patent No.: US 12,274,979 B2
(45) Date of Patent: Apr. 15, 2025

(54) FILTER UNIT FOR AIR CLEANING DEVICE, AND AIR CLEANING DEVICE

(71) Applicant: BSH Hausgeräte GmbH, Munich (DE)

(72) Inventors: Georg Hepperle, Heilbronn (DE); Daniel Vollmar, Pfinztal (DE)

(73) Assignee: BSH Hausgeräte GmbH, Munich (DE)

( * ) Notice: Subject to any disclaimer, the term of this patent is extended or adjusted under 35 U.S.C. 154(b) by 495 days.

(21) Appl. No.: 17/762,765

(22) PCT Filed: Nov. 4, 2020

(86) PCT No.: PCT/EP2020/080894
§ 371 (c)(1),
(2) Date: Mar. 23, 2022

(87) PCT Pub. No.: WO2021/099112
PCT Pub. Date: May 27, 2021

(65) Prior Publication Data
US 2022/0339577 A1    Oct. 27, 2022

(30) Foreign Application Priority Data

Nov. 19, 2019  (DE) .......................... 102019217831.6

(51) Int. Cl.
*B01D 53/32*    (2006.01)
*A61L 9/16*     (2006.01)
(Continued)

(52) U.S. Cl.
CPC .............. *B01D 53/323* (2013.01); *A61L 9/16* (2013.01); *B03C 3/019* (2013.01); *B03C 3/12* (2013.01);
(Continued)

(58) Field of Classification Search
CPC .......... B03C 3/019; B03C 3/12; B03C 3/155; A61L 9/16; A61L 2209/14; B01D 53/323;
(Continued)

(56) References Cited

U.S. PATENT DOCUMENTS 3,392,509 A * 7/1968 Pelosi, Jr. ................. B03C 3/49
                                                  96/66
3,763,633 A * 10/1973 Soltis ...................... B03C 3/155
                                                 55/528
(Continued)

FOREIGN PATENT DOCUMENTS

CN        106051912 A  * 10/2016
CN        106091109 A  * 11/2016
(Continued)

OTHER PUBLICATIONS

National Search Report CN 202080079909.4 dated Feb. 4, 2024.
International Search Report PCT/E P2020/080894 dated Feb. 5, 2021.

*Primary Examiner* — Christopher P Jones
*Assistant Examiner* — Sonji Turner
(74) *Attorney, Agent, or Firm* — Michael E. Tschupp; Andre Pallapies; Brandon G. Braun

(57) ABSTRACT

A filter unit for an air cleaning device includes an odor filter configured for odor neutralization and embodied as a device for plasma generation. The odor filter includes an air-permeable high-voltage electrode and an air-permeable counter electrode arranged behind one another in a direction of flow of air. Each of the air-permeable high-voltage electrode and the air-permeable counter electrode is formed by a panel element.

20 Claims, 13 Drawing Sheets

(51) Int. Cl.
  *B03C 3/019* (2006.01)
  *B03C 3/12* (2006.01)
  *B03C 3/155* (2006.01)

(52) U.S. Cl.
  CPC ........... *B03C 3/155* (2013.01); *A61L 2209/14* (2013.01); *B01D 2259/818* (2013.01)

(58) Field of Classification Search
  CPC .............. B01D 46/00; B01D 2257/708; B01D 2257/90; B01D 2258/06; B01D 2259/818; B01D 2259/4508; F24C 15/20; F24C 15/2035; F24C 15/2021
  See application file for complete search history.

(56) References Cited

U.S. PATENT DOCUMENTS

| | | | | |
|---|---|---|---|---|
| 4,549,887 | A * | 10/1985 | Joannou | B03C 3/14 96/58 |
| 5,108,470 | A * | 4/1992 | Pick | B03C 3/155 96/99 |
| 5,403,383 | A * | 4/1995 | Jaisinghani | B03C 3/155 95/79 |
| 5,807,425 | A * | 9/1998 | Gibbs | B03C 3/155 96/99 |
| 5,846,302 | A * | 12/1998 | Putro | B03C 3/155 96/99 |
| 6,955,708 | B1 * | 10/2005 | Julos | F24F 8/194 422/186.04 |
| 7,771,672 | B2 * | 8/2010 | Bergeron | A61L 9/015 422/186.04 |
| 8,003,058 | B2 * | 8/2011 | Bergeron | A61L 9/22 422/186.04 |
| 8,123,840 | B2 * | 2/2012 | Marra | B03C 3/155 95/59 |
| 8,834,799 | B2 | 9/2014 | Loreth | |
| 8,961,659 | B2 * | 2/2015 | McKinney | B03C 3/09 96/72 |
| 9,040,008 | B2 * | 5/2015 | Zahedi | B01D 53/323 588/900 |
| 10,766,039 | B2 | 9/2020 | Yuge | |
| 11,369,975 | B2 | 6/2022 | Hepperle | |
| 2008/0170971 | A1 | 7/2008 | Bergeron | |
| 2009/0199718 | A1 | 8/2009 | Tanaka | |
| 2009/0274592 | A1 * | 11/2009 | Bergeron | H01J 37/32568 422/186.04 |
| 2010/0089240 | A1 * | 4/2010 | Krichtafovitch | F24C 15/2035 96/95 |
| 2011/0094383 | A1 | 4/2011 | Noh | |
| 2011/0111691 | A1 | 5/2011 | Kagawa | |
| 2014/0219894 | A1 * | 8/2014 | Ikegami | B01D 53/8687 422/174 |
| 2015/0013541 | A1 | 1/2015 | Vandenbelt | |
| 2016/0175850 | A1 * | 6/2016 | Peczalski | B03C 3/014 95/57 |
| 2017/0014757 | A1 * | 1/2017 | Lin | A61L 9/015 |
| 2018/0347826 | A1 * | 12/2018 | Robison | F24C 15/205 |
| 2019/0193089 | A1 | 6/2019 | Takezawa | |
| 2020/0009577 | A1 * | 1/2020 | Hepperle | B03C 3/47 |

FOREIGN PATENT DOCUMENTS

| | | | |
|---|---|---|---|
| DE | 102017204061 A1 * | 9/2018 | .............. B03C 3/40 |
| DE | 102017214495 A1 * | 2/2019 | |
| EP | 0271457 A2 * | 6/1988 | |
| EP | 0403230 A1 * | 12/1990 | |

* cited by examiner

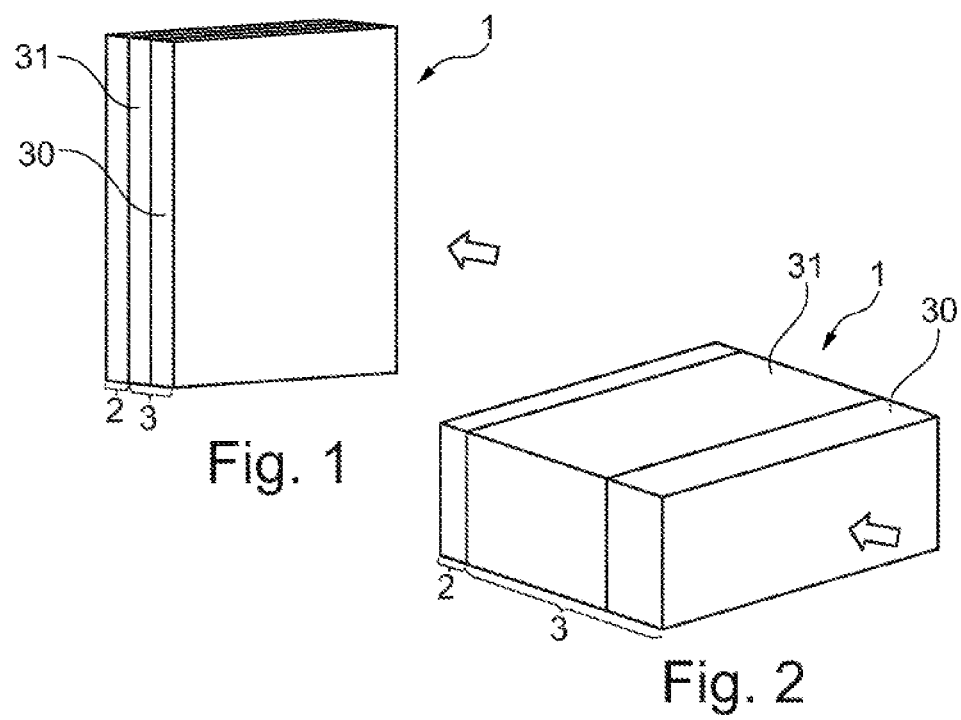

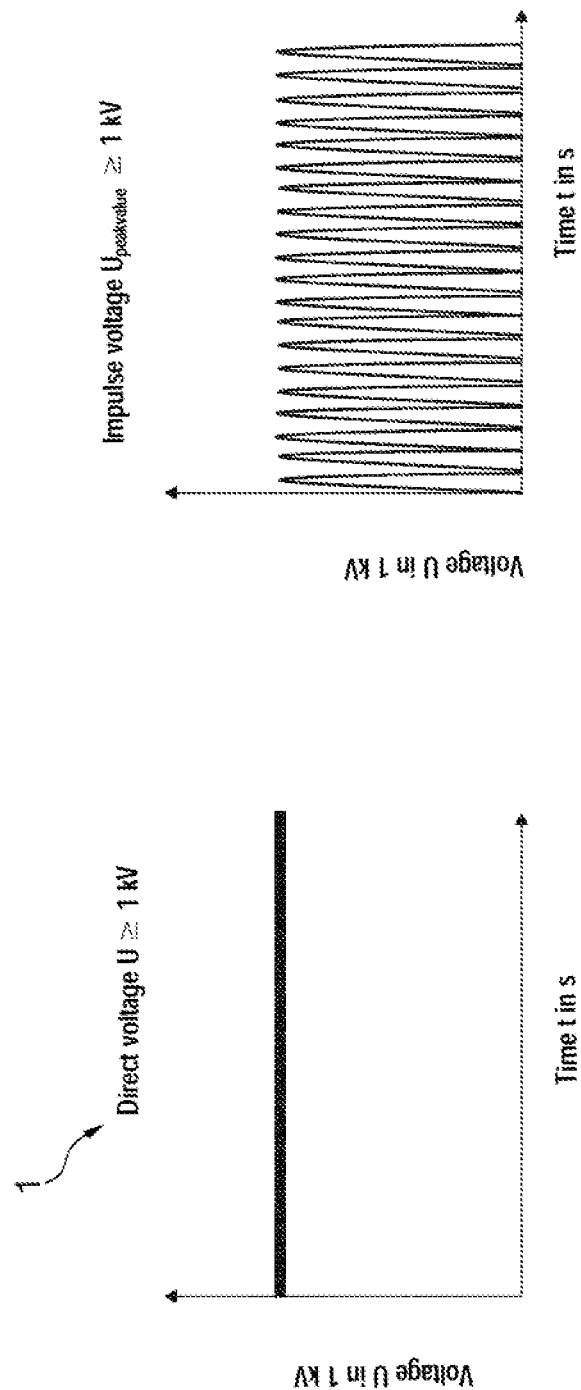

FILTER UNIT FOR AIR CLEANING DEVICE, AND AIR CLEANING DEVICE

CROSS-REFERENCES TO RELATED APPLICATIONS

This application is the U.S. National Stage of International Application No. PCT/EP2020/080894, filed Nov. 4, 2020, which designated the United States and has been published as International Publication No. WO 2021/099112 A1 and which claims the priority of German Patent Application, Serial No. 10 2019 217 831.6, filed Nov. 19, 2019, pursuant to 35 U.S.C. 119 (a)-(d).

The contents of International Application No. PCT/EP2020/080894 and German Patent Application, Serial No. 10 2019 217 831.6 are incorporated herein by reference in their entireties as if fully set forth herein.

BACKGROUND OF THE INVENTION

The present invention relates to a filter unit for an air cleaning device and to an air cleaning device.

In the specific case of vapor extractors that are used in recirculating mode, the filter efficiency of the installed filter media is largely responsible for the extent to which the steam from cooking, permeated by extremely fine particles and cooking odors, is filtered. This is relevant in so far as the steam that is sucked in by the vapor extractor is not transported outside into the open environment, but is recirculated in the enclosed space (living space, kitchen, etc.). If the filter media installed in the vapor extractor have a low or unsatisfactory filter efficiency, the cooking vapors consisting of an aerosol and olfactorily unpleasant volatile organic compounds remain in the enclosed air of the living space. In this context, high demands in respect of filter efficiency are placed on the filter media installed in the vapor extractor. The purpose of the invention is to maintain clean air in both living spaces and passenger compartments of motor vehicles.

In vapor extractors, mechanical filters are employed for the purpose of filtering out aerosols (solid and liquid particles). These include expanded metal filters, perforated sheet filters, baffle filters, nonwoven fabrics (fibrous material), edge suction filters, sintered plastics and other porous media or the like. All of these filter media use mechanical separation mechanisms for filtering, such as the diffusion effect, blocking effect and particularly the inertia effect. When using the inertia effect for the purpose of separation, the particle is not able to follow the streamline of the gas (air) around the individual filter fibers, expanded metal layers, porous media or similar due to its mass inertia, and therefore collides with them. With regard to the odor filtration of cooking odors and other volatile organic compounds (VOCs), active carbon filters and zeolite filters (also referred to as recirculation filters for vapor extractors in practice) in the form of filter cartridges are generally used for the recirculating mode in practice. These are usually installed directly behind the grease filter (but ahead of the fan) or in the exhaust zone of the vapor extractor behind the fan. In addition to the cited adsorbents, use is also made of plasma filters in practice, these being employed as independent systems for neutralizing odor. These systems, generally considered add-on parts, are installed as a fixture on the exhaust connection piece (behind the fan) of the vapor extractor. These plasma filters normally have a cylindrical structure for attachment to the air outlet connection piece of the fan housing.

In the systems described above, it is significant that the grease filter and the odor filter or odor neutralization system (plasma filter) are spatially separate from each other along the airflow path. A further disadvantage of existing plasma filters is that they require a relatively large amount of room or structural space and cannot be combined with all types of vapor extractor. Furthermore, both the adsorbers (active carbon filters, zeolite filters) and plasma filters are systems that cannot normally be cleaned. Recyclable systems are rarely available on the market. The service life of these odor filters or systems for odor neutralization (plasma filters) is shorter than a standard commercial vapor extractor.

BRIEF SUMMARY OF THE INVENTION

The object of the invention is therefore to provide a solution which has a modest space requirement and whereby sufficient filter efficiency can be reliably guaranteed.

According to a first aspect, the invention therefore relates to a filter unit for an air cleaning device, said filter unit comprising an odor filter, in the form of a device for plasma generation, for odor neutralization. The filter unit is characterized in that the odor filter comprises at least one air-permeable high-voltage electrode and at least one air-permeable counter electrode, each of these forming a free surface, and that the at least one air-permeable high-voltage electrode and the at least one air-permeable counter electrode are arranged one behind the other in the direction of flow.

The filter unit is also referred to in the following as a filter module or filter cartridge. The air cleaning device in which the filter unit may be used can be a vapor extraction device or vapor extractor or other vapor suction device or an air cleaner for interiors or passenger compartments in motor vehicles.

The odor filter for odor neutralization is also referred to in the following as a plasma filter, plasma unit, plasma module or plasma segment. The plasma filter is used to remove volatile organic compounds (VOCs) from the airstream that is drawn in.

According to the invention, the plasma filter has at least one air-permeable high-voltage electrode and at least one air-permeable counter electrode. The electrodes of the plasma filter are panel elements in each case. The at least one air-permeable high-voltage electrode and the at least one air-permeable counter electrode are arranged one behind the other in the direction of flow. The direction of flow refers to the direction in which air that is drawn in flows through the filter unit. The format of the high-voltage electrode and the counter electrode, i.e. the panel elements, can be a flat surface area. Alternatively, the panel element can also have a rounded, wavy or pleated format. The electrodes of the plasma filter preferably lie parallel to each other. When using electrodes in the form of a panel element that does not have a flat surface area, the format of the high-voltage electrode(s) and the counter electrode(s) is identical, i.e. their curvature, curvature of the individual waves or rise of the pleated peaks is identical. It is thereby possible to ensure that the distance between the electrodes is identical over the surface area of the electrodes. During operation of the filter unit, a plasma is generated between the high-voltage electrode and the counter electrode.

Concerning the voltage waveform that is applied to the electrodes of the odor filter, one possibility for the air-permeable high-voltage electrode is an impulse voltage with e.g. $U_{peakvalue} >= 500$ V and a cycle duration $T <= 1$ s. The impulse voltage can be a positive or negative voltage type.

Alternatively, a further possibility is an alternating voltage with e.g. $U_{effectivevalue} >= 500$ V and a cycle duration $T >= 1$ s. Various voltage waveforms are possible for the alternating voltage and the impulse voltage. For example, a sinusoidal, rectangular, triangular or sawtooth voltage waveform can be used.

The air-permeable counter electrode is connected to the electrical counter potential, so that a changing electrical voltage difference ΔU can be guaranteed between the high-voltage electrode and the counter electrode. Alternatively, the air-permeable counter electrode can be grounded. For this, the air-permeable counter electrode is electrically connected to the protective conductor PE (protective earth).

Since the electrodes take the form of a panel element in each case, a plasma wall is formed in the interval between the electrodes, and the impure air passes through said plasma wall and is cleaned there.

By virtue of the high-voltage electrode and the counter electrode being air-permeable and arranged one behind the other in the direction of flow, it is possible to achieve a range of advantages. In particular, a high level of efficiency can be achieved in respect of the odor reduction. This is because a plasma wall is produced by means of the at least one air-permeable high-voltage electrode and the at least one air-permeable counter electrode during operation, and the air that is laden with odor molecules flows through said plasma wall. When the airborne odor molecules flow through this ionization zone or "plasma wall", these odor molecules undergo a complete chemical reaction with the reactive species. In other words, a complete intermixture of odor molecules and other reactive oxygen species (ROS) and reactive nitrogen species (RNS) occurs.

According to a preferred embodiment variant, the filter unit has an electrostatic filter comprising an ionization unit and a separation unit. The electrostatic filter serves to filter out particles or so-called aerosols such as e.g. grease, water or dirt from the air. The electrostatic filter is also referred to as an electrostatic particle filter, particle filter or grease filter. The electrostatic filter has an ionization unit which is also referred to as an ionization stage or ionization segment. Particles are charged in the ionization unit, e.g. by means of the so-called corona discharge. To this end, provision is preferably made for at least one emission electrode and at least one counter electrode in the ionization unit. Most preferably, an emission electrode is provided in each case between two counter electrodes of the ionization unit. The particles that are to be separated in the electrostatic filter have no electrical charge or insufficient electrical charge in their original state for an efficient electrostatic separation. By means of the ionization unit, electrical particle charging of each individual particle is effected, preferably up to its maximum electrical saturation charge $q_s$. The emission electrode, which can take the form of e.g. a wire, is preferably exposed to an electrical high voltage in this case. The voltage can be either a positive or a negative voltage. A positive electrical voltage is preferred on the basis of lower ozone emission. The voltage waveform can be e.g. a direct voltage with e.g. $U >= 1$ kV DC, or alternatively an impulse voltage with e.g. a voltage $U_{peakvalue} >= 1$ kV and a cycle duration $T <= 1$ s. The impulse voltage can have a sinusoidal, rectangular, triangular or sawtooth voltage waveform. The counter electrodes of the ionization unit are preferably electrically connected to the electrical counter potential. According to an embodiment variant, the counter electrodes of the ionization unit are connected to the protective conductor PE (protective earth).

As an alternative to the described ionization unit for particle charging, which works according to the principle of corona discharge, it is also possible to use an ionization unit in which a different mechanism is applied for the purpose of particle charging. This includes an ionization unit in which the particle charging is effected by means of dielectrically impeded barrier discharge (DBD) or photoemission.

The particles that have been electrically charged by the ionization unit flow through the separation unit, which can also be referred to as the separation segment and is arranged downstream of the ionization unit in the direction of flow. In the separation unit, at least two collecting electrodes which are exposed to an electrical high voltage together form an electrical field. The air with the electrically charged particles emerging from the ionization unit flows into the separation unit. As a result of the electrical field that is formed there between the collecting electrodes, the particles are separated at the collecting electrodes and thereby filtered out of the air.

By virtue of the filter unit having an electrostatic filter in addition to the odor filter, this embodiment variant combines the function of a particle filter and an odor filter in one system, i.e. in one filter unit. By means of this embodiment variant, the air is cleaned of all types of impurities.

According to an embodiment variant, the separation unit of the electrostatic filter has at least one live collecting electrode and at least one grounded collecting electrode. The collecting electrodes here are preferably arranged in an alternating manner in the separation unit. According to an embodiment variant, the collecting electrodes of the separation unit can be air-impermeable plates. In this case, the separation unit can also be referred to as a plate separator. An electrical field strength E (=voltage/plate distance) forms between the plates arranged in an alternating manner during operation of the filter, and this in turn exerts an external force on the charged particle in each case. As a result, the charged particle is deflected towards the collecting electrodes and separated thereon. The particles collect on the surface of the plates. The plates are preferably arranged parallel to the flow direction of the air through the filter unit.

According to an alternative embodiment variant, the collecting electrodes take the form of air-permeable electrodes. In this case, the particle separation takes place at the live air-permeable collecting electrodes and the grounded air-permeable collecting electrodes, these likewise being alternately arranged. The collecting electrodes are preferably embodied as panel elements, e.g. as flat panel elements. In the case of air-permeable collecting electrodes, these are preferably arranged in an orientation which is inclined relative to the direction of flow and is preferably perpendicular to the direction of flow.

According to a preferred embodiment variant, the odor filter of the filter unit is arranged downstream of the electrostatic filter in the direction of flow. This ensures that the impure air, in particular the cooking vapor, is initially cleared of particles, in particular aerosols, before the odors contained in the air, in particular cooking odors, are then neutralized. Alternatively, the odor filter can also be spatially arranged between the segments of the electrostatic filter, i.e. between the ionization segment and the separation segment. In a further alternative, the odor filter is arranged upstream of the electrostatic filter in the direction of flow, in particular upstream of the ionization unit.

According to an embodiment variant, the odor filter and the electrostatic filter are arranged in a shared housing. The housing can also be referred to as a frame. The segments of the filter unit, in particular the ionization segment, the separation segment and the odor filter, are preferably contained in the housing in such a way that they can be removed. In this type of configuration, all three segments can be withdrawn individually from the housing. It is however also possible for the segments of the electrostatic filter to be connected together such that they can only be withdrawn from the housing jointly, while the odor filter can be withdrawn from the housing separately from the electrostatic filter. In the case of segments that are removably contained, the housing can be permanently secured in the air cleaning device. The segments of the filter unit can however also be permanently connected in the housing. In this case, the housing is preferably held in the air cleaning device in such a way that it can be removed. By this means, the odor filter and the electrostatic filter can be withdrawn from the air cleaning device together. However, the housing can be permanently held in the air cleaning device in this case likewise. Each segment optionally has a separate filter housing. These are then positively, non-positively or materially interconnected.

The withdrawal of one or more segments of the filter unit may be necessary for maintenance or cleaning purposes, for example. In the case of positive or non-positive connection between individual filter housings, the segments can be disassembled by the user for maintenance or cleaning purposes.

According to a preferred embodiment variant, the electrodes of the odor filter are arranged in an orientation which is inclined relative to the main direction of flow. The electrodes of the odor filter are preferably perpendicular to the direction of flow. By virtue of this orientation of the electrodes, it is possible firstly to maximize the surface area of the plasma wall produced by the electrodes without having to increase the depth of the filter unit, i.e. the dimension thereof in the direction of flow. Secondly, it is possible using this orientation to ensure that the air to be cleaned flows through the air-permeable electrodes and that the air is thereby intermixed, whereby an efficient depletion of odor molecules and other VOCs is ensured even in the case of a modest energy input.

At least one of the electrodes of the odor filter preferably has an insulation coating on at least one surface.

According to the invention, the active mechanism of the odor filter for eliminating odors is the concept of the dielectric impeded barrier discharge (DBD). The insulation coating that is provided on at least one electrode of the odor filter can therefore function as a dielectric between the high-voltage electrode and the counter electrode.

The capacitive odor filter arrangement consisting of at least two electrodes (high-voltage electrode, counter electrode) with different electrical voltage potentials from each other and at least one dielectric between said two electrodes, when a temporally changing electrical voltage difference $\Delta U$ is implemented between said two electrodes, results in an electrical displacement current I which in turn causes an ionization of the air as a result of the ionization processes. Due to this ionization process in the ionization zone (plasma zone), reactive species are formed as a result of impact ionization processes, namely reactive oxygen species (ROS) and reactive nitrogen species (RNS). These reactive species are energetically highly reactive molecules which enter into chemical compounds with inter alia unpleasant odor molecules and other volatile organic compounds (VOCs), whereby these unpleasant odor molecules are chemically transformed into other chemical compounds. By means of chemical processes between the odor molecules and the reactive species, odors are consequently reduced or even eliminated completely.

In accordance with this process/manner of functioning, provision is made for porous electrodes in the odor filter (i.e. in the segment for odor neutralization), which cause an ionization of the air between the electrodes in accordance with the principle of the dielectrically impeded barrier discharge. This ionization of the air in the ionization zone (plasma formation) results in the depletion/neutralization of olfactorily unpleasant odor molecules and other volatile chemical compounds (VOCs).

For this reason, at least one of the two electrodes of the odor filter has an electrical surface insulation (a dielectric) in order to prevent electrical arcing and short circuits between the two electrodes and to support the function of the plasma unit. Ideally, the air-permeable high-voltage electrode is so made as to be electrically insulating. Alternatively, the air-permeable counter electrode can be so made as to be electrically insulating or all electrodes can have an electrical insulation on their surface.

Possible coating methods for electrically insulating the odor filter electrode(s) include e.g. functional powder and ceramic coatings, fluidized-bed coating methods, sol-gel methods, dip coating, enameling, painting or rubber coating of the electrode(s).

The electrodes of the odor filter are preferably arranged alternately in relation to each other. This means that an air-permeable high-voltage electrode is provided for each air-permeable counter electrode. The first and last electrode in the direction of flow can be either an air-permeable counter electrode or an air-permeable high-voltage electrode.

According to an embodiment variant, at least one high-voltage electrode and/or at least one counter electrode has a multilayered structure. In this embodiment variant, the respective electrode consists of a plurality of air-permeable layers ($n >= 1$).

According to the invention, the electrodes of the odor filter are air-permeable. According to an embodiment variant, the at least one high-voltage electrode and the at least one counter electrode consist of an air-permeable material. In this embodiment variant, the electrodes are also referred to as porous electrodes. The electrodes can all consist of the same air-permeable material. It is however also within the scope of the invention for different electrodes to consist of different materials. Using an air-permeable material for the electrodes of the odor filter has the advantage that the manufacture of the odor filter is simplified since the required air permeability is provided by the material itself.

According to a further embodiment variant, the electrodes of the odor filter consist of an air-impermeable material having at least one air conduction opening. It is also possible for only some of the electrodes, e.g. only the high-voltage electrodes or only the counter electrodes, to consist of such a material and for the other electrodes to consist of an air-permeable material.

Irrespective whether the electrodes of the odor filter consist of an air-permeable material or an air-impermeable material with air conduction openings, the material of the electrodes is so selected as to be electrically conductive or antistatic.

For example, the electrodes of the odor filter can be perforated sheet metal, e.g. perforated plate, welded mesh, woven wire netting, expanded metal, sintered materials and foamed material.

The electrodes of the odor filter are preferably so arranged as to be offset relative to each other in order to ensure optimal ionization of the air which flows through and is laden with odor molecules, thereby in turn ensuring optimal neutralization of the odorous substances/odor molecules. An offset arrangement refers to an arrangement in which the openings in an electrode do not coincide with the openings of an adjacent electrode.

According to an embodiment variant, a high-voltage electrode and a counter electrode are arranged relative to each other in such a way that their structure is rotated about an axis in the plane of the respective electrode. This means that the individual electrodes in the plane of the respective electrode are offset in the installed state by an angle of 0 to 360° about an axis of rotation which is perpendicular to the plane of the electrode.

According to a preferred embodiment variant, the electrodes of the odor filter are exposed to a high voltage which changes over time. The high voltage can be an alternating voltage or an impulse voltage, for example. According to an embodiment variant, the odor filter therefore has a high-voltage transformer by means of which a temporally changing high voltage can be generated for the electrodes of the odor filter, in particular the high-voltage electrode of the odor filter. The high-voltage transformer is used in this case to generate or produce the required electrical high voltage. The high-voltage transformer can also be referred to as a high-voltage generator or high-voltage power supply. This high-voltage transformer supplies the electrodes of the odor filter, in particular the at least one high-voltage electrode and at least one counter electrode, with electrical high voltage or electrical energy via the power cables on the secondary side. On the primary side, the electrical voltage supply to the high-voltage transformer is effected via a connection interface or a power cable for lower voltage. This lower voltage on the primary side of the high-voltage transformer can be a direct voltage of <=1500 V DC or an alternating voltage of <=1000 V AC.

According to a further aspect, the present invention relates to an air cleaning device which has at least one filter unit according to the invention.

Advantages and features that are described in relation to the filter unit are correspondingly valid (if applicable) in relation to the air cleaning device and vice versa.

The air cleaning device can be e.g. an air cleaner for filtering room air, a device for filtering air that is drawn into a passenger compartment of a motor vehicle, or a vapor extractor for kitchens. According to the invention, the air cleaning device can have a plurality of inventive filter units. The at least one filter unit is preferably arranged on the suction side of the air cleaning device. It is however also within the scope of the invention additionally or alternatively to provide at least one filter unit on the air outlet side of the air cleaning device.

According to a preferred embodiment variant, the air cleaning device takes the form of an extractor hood and the at least one filter unit is arranged ahead of the fan of the vapor extraction device.

With reference to the vapor extractor, the inventive filter unit, which can also be referred to as an ionizing filter unit/filter cartridge, is preferably arranged in the air intake zone of the vapor extractor so that those components of the vapor extractor situated behind said filter unit are not contaminated with cooking steam/aerosols/dirt. However, such an ionizing filter unit can optionally also be arranged in the vapor stream at the air outlet zone, or along the airflow path between the inlet zone and outlet zone of the vapor extractor. The geometric dimensions (length, width and height) of such an ionizing filter module vary according to the mounting location or the type and geometry of the vapor extractor.

BRIEF DESCRIPTION OF THE DRAWINGS

The invention is described again in greater detail with reference to the appended figures, in which:

FIG. 1 shows a schematic perspective view of an embodiment variant of the filter unit according to the invention;

FIG. 2 shows a schematic perspective view of a further embodiment variant of the filter unit according to the invention;

FIGS. 11a to 11d show schematic illustrations of possible voltage profiles of the voltage for the odor filter of the filter unit according to the invention;

DETAILED DESCRIPTION OF EXEMPLARY EMBODIMENTS OF THE PRESENT INVENTION

Figure 3:
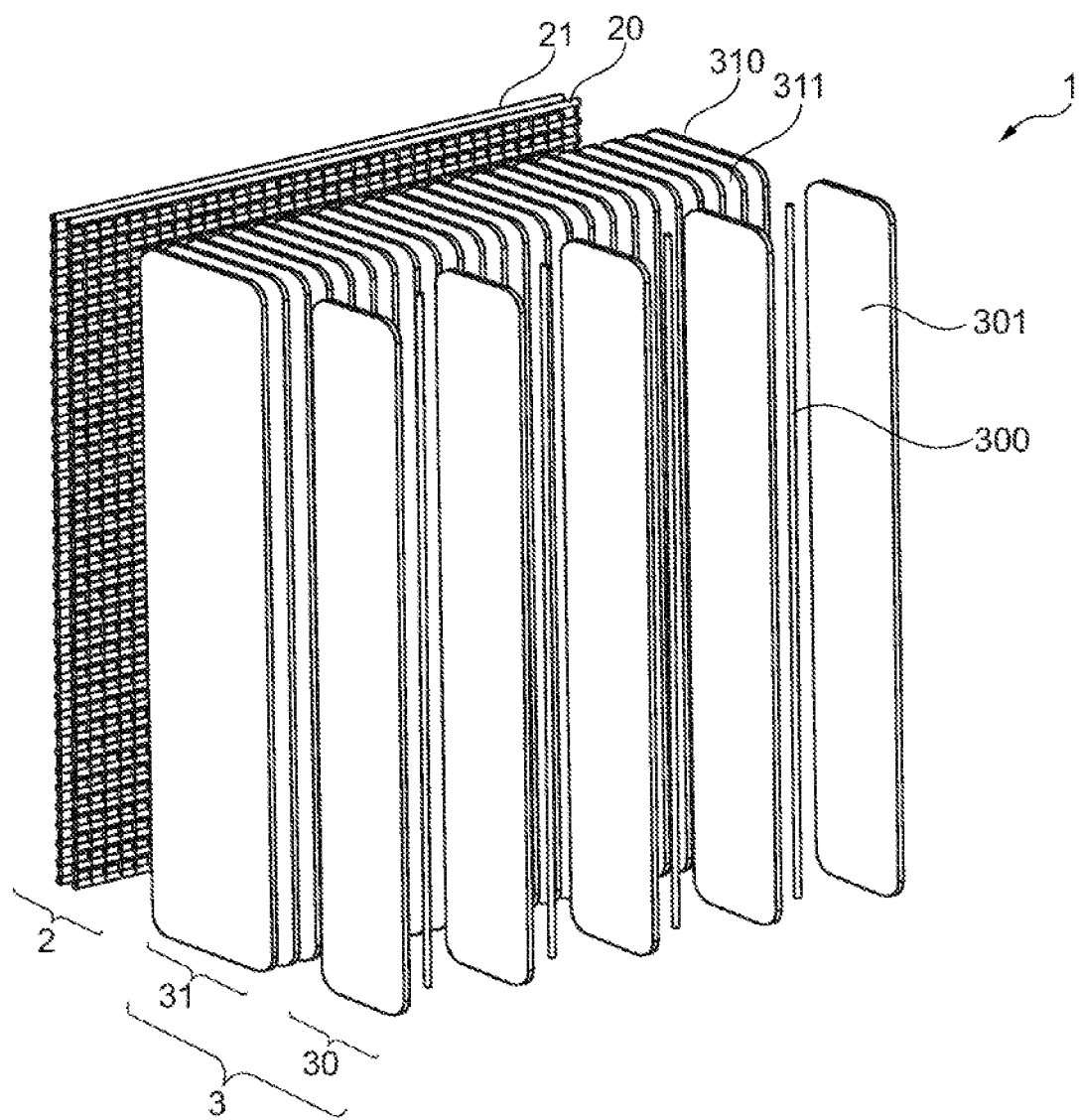
FIG. 3 shows a schematic perspective exploded view of an embodiment variant of the filter unit according to the invention.

FIG. 1 shows a schematic perspective view of a first embodiment variant of the filter unit 1 according to the invention. The filter unit takes the form of an electrically ionizing filter unit 1 and is also referred to as a filter module/filter cartridge. The filter unit 1 consists of an odor filter 2, which is also referred to as a plasma filter, and an electrostatic filter 3. The function of the electrostatic filter 3 is to filter out solid and liquid particles (aerosols) from the airstream. The plasma filter 2 connected downstream thereof is used for odor neutralization of cooking odors and other VOCs in the airstream. The cited electrically ionizing filter module 1 consists of three segments as per FIG. 1. In particular, the filter unit 1 consists of a segment for particle charging which is also referred to as an ionization unit 30, a segment for particle separation which is also referred to as a separation unit 31, and the segment for odor neutralization which is also referred to as an odor filter 2 or plasma filter. All three segments 30, 31, 2 are spatially arranged one behind the other in the direction of air flow, this being indicated by a block arrow in the figures, and outwardly appear as an autonomous filter system.

Concerning the orientation of the individual segments 30, 31, 2 along the direction of air flow, the segment for particle charging 30 is arranged ahead of the segment for particle separation 31 in FIG. 1. The segment for odor neutralization 2 by means of plasma is preferably the last air treatment stage. This ensures that aerosols are filtered out of the cooking steam first, and the cooking odors are then neutralized. Alternatively, the segment for odor neutralization can also be spatially arranged between the other two segments or even in the first position ahead of the segment for particle charging.

FIG. 2 shows a further embodiment variant of the filter unit 1. This only differs from the embodiment variant shown in FIG. 1 in respect of the depth of the individual segments, i.e. their extent in the direction of flow.

The individual parts of the individual segments 2, 30, 31 of an embodiment variant of the filter unit 1 are illustrated in FIG. 3. For the purpose of particle filtration in the embodiment variant according to FIG. 3, use is made of an electrostatic filter 3 composed of the segment for particle charging 30 and the segment for particle separation 31. The particle charging is effected in the ionization unit 30 by means of a corona discharge. For this purpose, an emission electrode 300 is arranged in each case between two counter electrodes 301. In the ionization unit 30, the particles (solid and liquid) contained in the air are electrically charged by means of the corona discharge. In this case, the electrical particle charging of each individual particle is preferably achieved up to its maximum electrical saturation charge $q_s$ in the ionization unit 30.

Figure 11D:
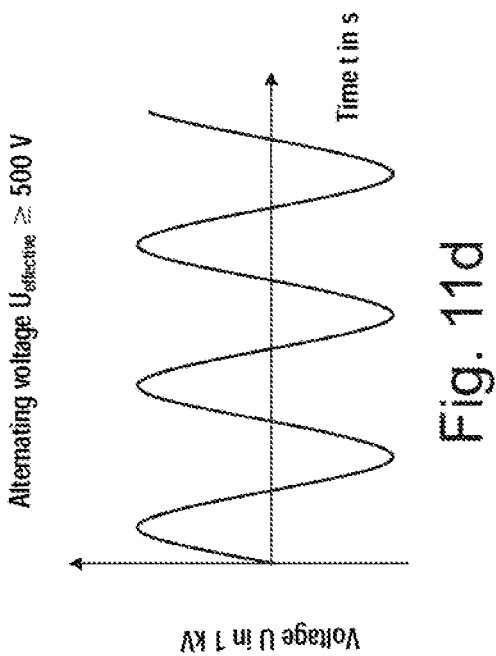

The emission electrode 300 is exposed to an electrical high voltage in this case. Concerning said electrical voltage, either positive or negative voltage can be applied. A positive electrical voltage is preferred on the basis of the lower ozone emission. Concerning the voltage waveform, use can be made of either direct voltage with $U >= 1$ kV DC (direct current) (see FIG. 11a) or alternatively impulse voltage with $U_{peakvalue} >= 1$ kV (see FIG. 11b) and a cycle duration $T <= 1$ s. The impulse voltage can have a sinusoidal, rectangular, triangular or sawtooth voltage waveform. The grounded counter electrodes 301 are electrically connected to the electrical counter potential, to the protective conductor PE (protective earth) in this embodiment variant. Alternatively, it is also possible to apply a further mechanism for particle charging, which differs from the described principle of corona discharge, in the ionization unit 30 for the purpose of particle charging. Possibilities include particle charging by means of the dielectrically impeded barrier discharge (DBD) or photoemission.

The electrically charged particles then flow through the separation unit 31. The separation unit 31 takes the form of a plate separator in the embodiment variant according to FIG. 3. In the embodiment variant according to FIG. 4, the separation unit 31 is alternatively constructed using an air-permeable separation medium in the form of air-permeable electrodes 312, 313. Both options are possible and can be applied for the purpose of particle separation in the ionizing filter unit 1 according to intended use.

The plate separator is composed of at least one live plate-form collecting electrode plate 310 and at least one grounded plate-form collecting electrode plate 311, these being arranged alternately in each case. An electrical field strength E (=voltage/plate distance) forms between the alternately arranged plates 310, 311 during operation of the filter, and this in turn exerts an external force on the charged particle in each case. As a result, the charged particle is deflected towards the collecting electrodes 310, 311 and separated thereon. The particles collect on the surface of the plates 310, 311.

In the case of an air-permeable separation medium (see FIG. 4), the particle separation takes place at the live air-permeable collecting electrodes 312 and grounded air-permeable collecting electrodes 313, these being alternately arranged likewise. The illustrated air-permeable collecting electrodes 312, 313 can in principle be made of any air-permeable material/medium. Possible examples include welded mesh, wire cloth, fibrous materials, perforated plate, expanded metal, sintered plastics and foamed material or similar air-permeable media. If porous plastic media are used, they must be made in such a way as to be electrically conductive in respect of their specific properties, so that the electrical field can be established between the individual layers.

Concerning the voltage type, a positive or negative voltage can be used for the live collecting electrode plate 310 or the live air-permeable collecting electrode 312. Concerning the voltage waveform, it is possible to use either direct voltage with $U >= 1$ kV DC (see FIG. 11a) or alternatively impulse voltage with $U_{peakvalue} >= 1$ kV (see FIG. 11b) and a cycle duration $T <= 1$ s. The impulse voltage can have a sinusoidal, rectangular, triangular or sawtooth voltage waveform. The grounded collecting electrode plate 311 and the grounded air-permeable collecting electrode 313 respectively are electrically connected to the counter potential, here the protective conductor interface PE (protective earth).

Figure 4:
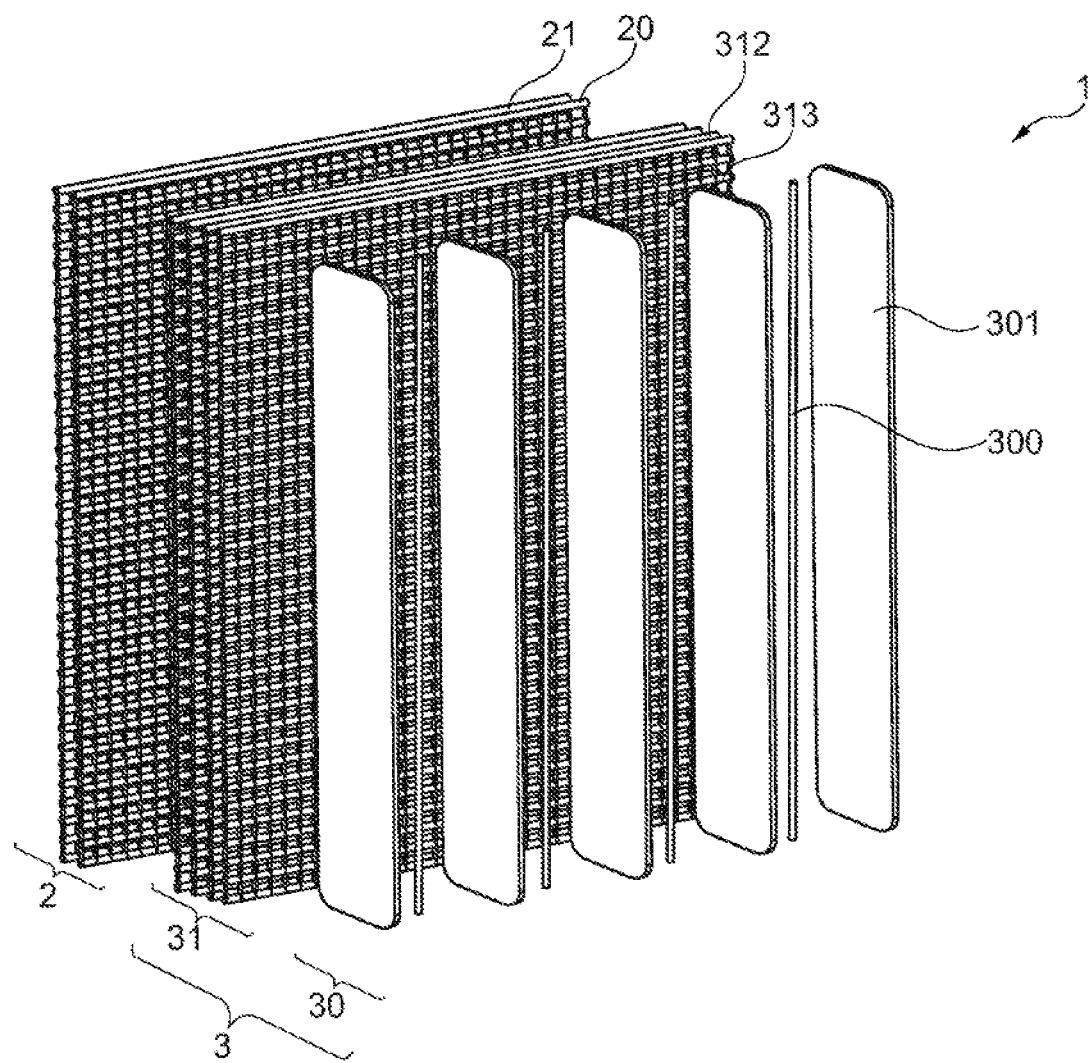
FIG. 4 shows a schematic perspective exploded view of a further embodiment variant of the filter unit according to the invention.

The plasma filter 2 as per FIG. 3 and FIG. 4 consists of at least one air-permeable high-voltage electrode 20 ($n >= 1$) and at least one air-permeable counter electrode 21 ($n >= 1$). The porous electrodes 20, 21 illustrated in FIG. 3 and FIG. 4 can in principle be made of any material/medium which is air-permeable and electrically conductive or antistatic. Possible examples include perforated sheet metal, e.g. perforated plate, welded mesh, woven wire netting, expanded metal, sintered materials and foamed material.

Figure 8A:
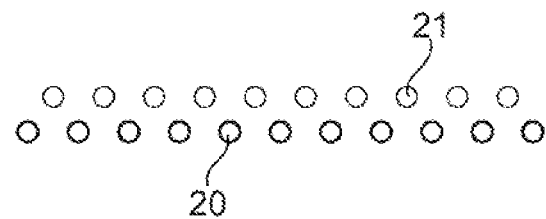
FIGS. 8a, 8b and 8c show schematic illustrations of an embodiment variant of the electrode geometry of the odor filter of the filter unit according to the invention.
Figure 8B:
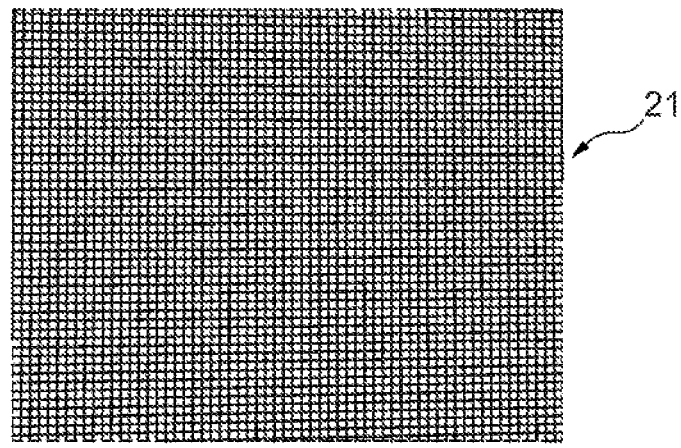
Figure 8C:
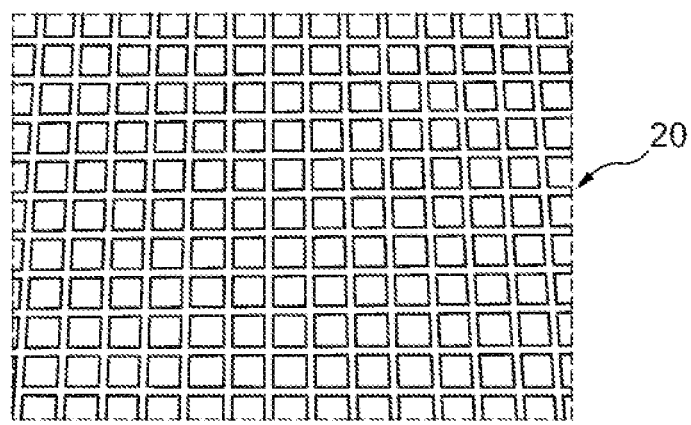
Figure 9A:
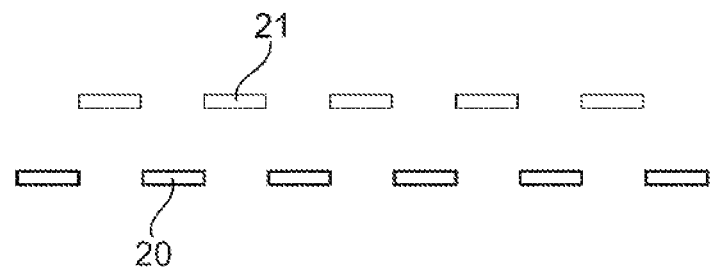
FIGS. 9a and 9b show schematic illustrations of a further embodiment variant of the electrode geometry of the odor filter of the filter unit according to the invention.
Figure 9B:
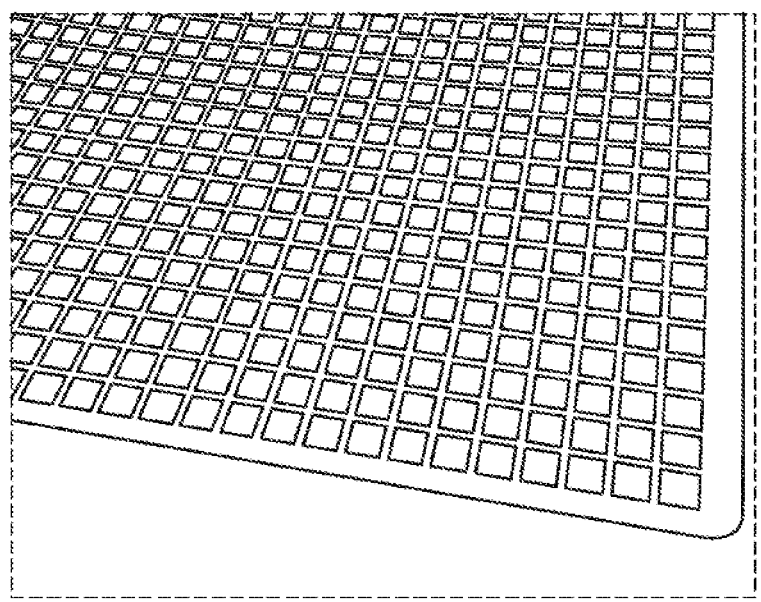
Figure 10A:
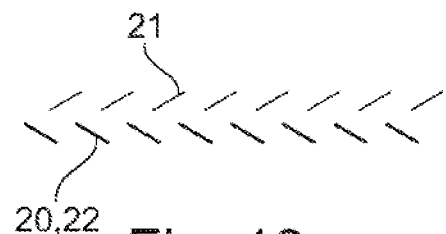
FIGS. 10a, 10b and 10c show schematic illustrations of a further embodiment variant of the electrode geometry of the odor filter of the filter unit according to the invention.
Figure 10B:
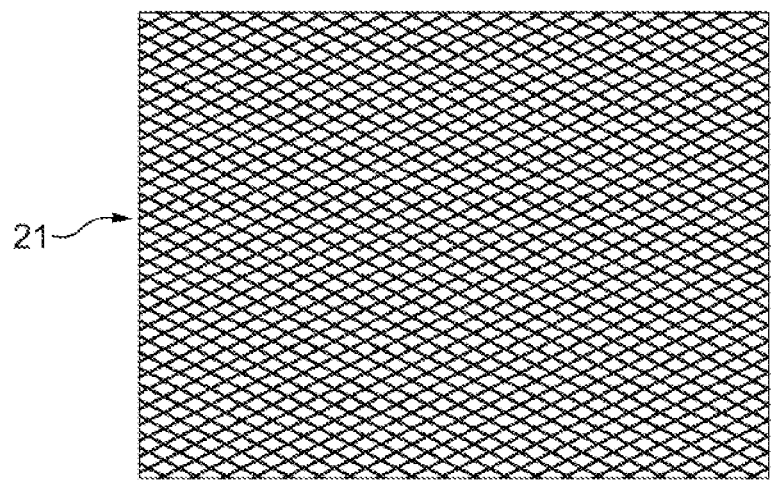
Figure 10C:
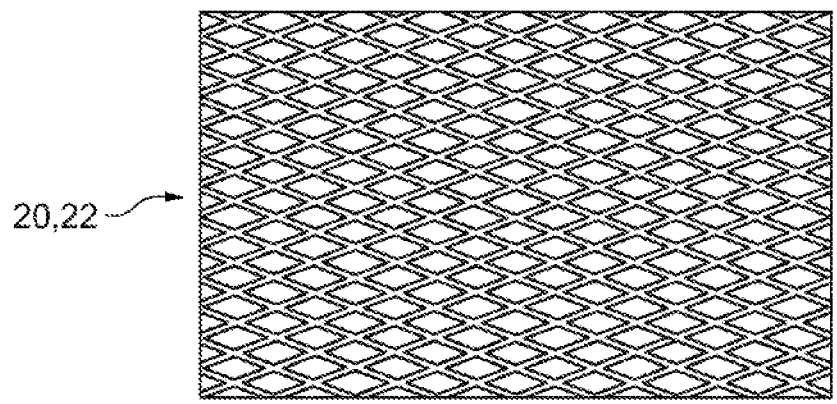

For a better understanding, such geometries of the electrodes of the odor filter 2 are partially illustrated in FIGS. 8 to 10. In FIG. 8a, the air-permeable counter electrode 21 is formed by a woven wire netting which is shown in FIG. 8b. The air-permeable high-voltage electrode 20 in the embodiment variant according to FIG. 8a is formed by a welded mesh which is shown in FIG. 8c. The welded mesh is electrically insulated. In FIG. 9a, the air-permeable counter electrode 21 and the air-permeable high-voltage electrode 20 are each formed by a perforated plate which is shown in FIG. 9b. The perforated plate which forms the air-permeable high-voltage electrode 20 is preferably electrically insulated. In FIG. 10a, the air-permeable counter electrode 21 and the air-permeable high-voltage electrode 20 are each formed by an expanded metal. The expanded metal forming the air-permeable counter electrode 21 is shown in FIG. 10b and the expanded metal forming the air-permeable high-voltage electrode 20 is shown in FIG. 10c and is electrically insulated.

If plastic media are used as air-permeable material for the electrodes 20, 21 of the odor filter 2, at least one must be made in such a way as to be electrically conductive or antistatic having a surface resistance $R <= 10^{11}$ Ohms in respect of its specific properties, so that an electrical field can be established when an electrical voltage difference $\Delta U$ is applied between the electrodes 20, 21 and ionization takes place.

Figure 12A:
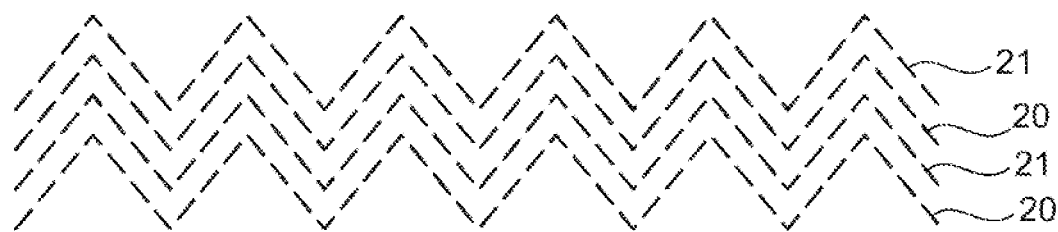
FIGS. 12a and 12b show schematic illustrations of different geometries of the electrodes of the odor filter.
Figure 12B:
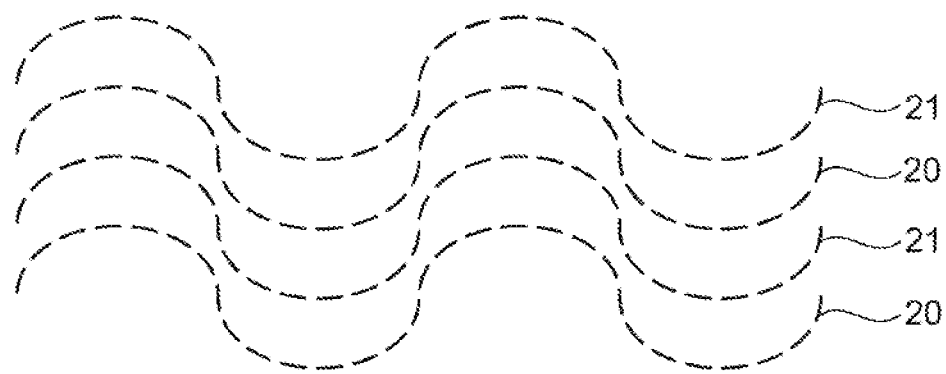

FIGS. 12a and 12b show further embodiment variants of the geometry of the electrodes of the odor filter. In FIG. 12a, each of the electrodes 20, 21 is pleated. In FIG. 12b, each of the electrodes 20, 21 has a wavy structure. Although the distance between the electrodes 20, 21 varies in FIG. 12b, the distance is preferably identical over the surface area of the electrodes.

Figure 5:
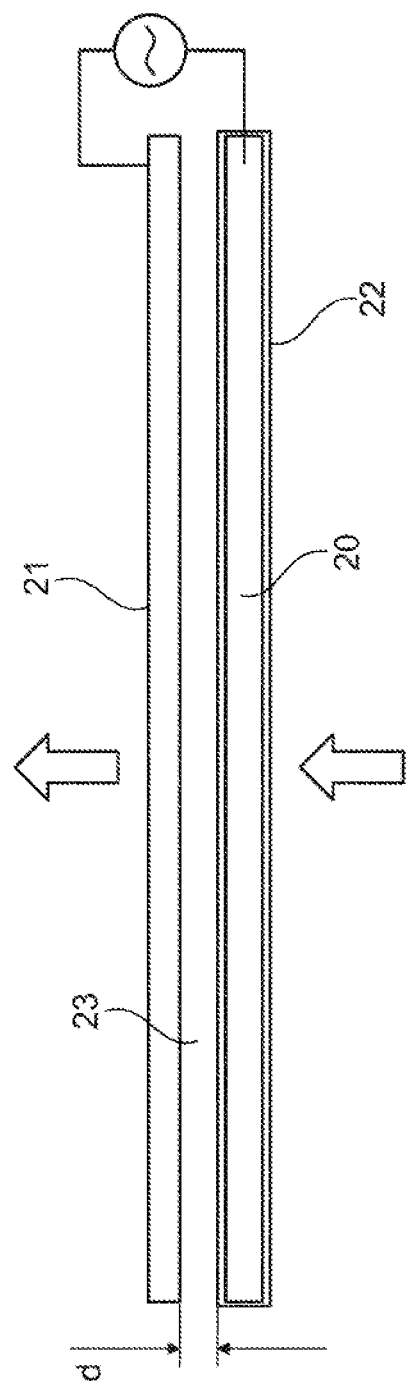
FIG. 5 shows a schematic block diagram of an embodiment variant of the odor filter of the filter unit according to the invention.

FIG. 5 schematically shows the structure of the odor filter in a block diagram. The interval/distance d between the air-permeable counter electrode 21 and the air-permeable high-voltage electrode 20 is >=0 mm. The distance d is preferably between 0 and 6 mm. The distance is dependent on the magnitude of the electrical voltage applied to the live electrode 20. The plasma forms in the ionization zone 23 between the air-permeable counter electrode 21 and the air-permeable high-voltage electrode 20. The air-permeable high-voltage electrode 20 is provided with an insulation coating 22 which forms the dielectric and can also be referred to as sheathing.

Figure 6:
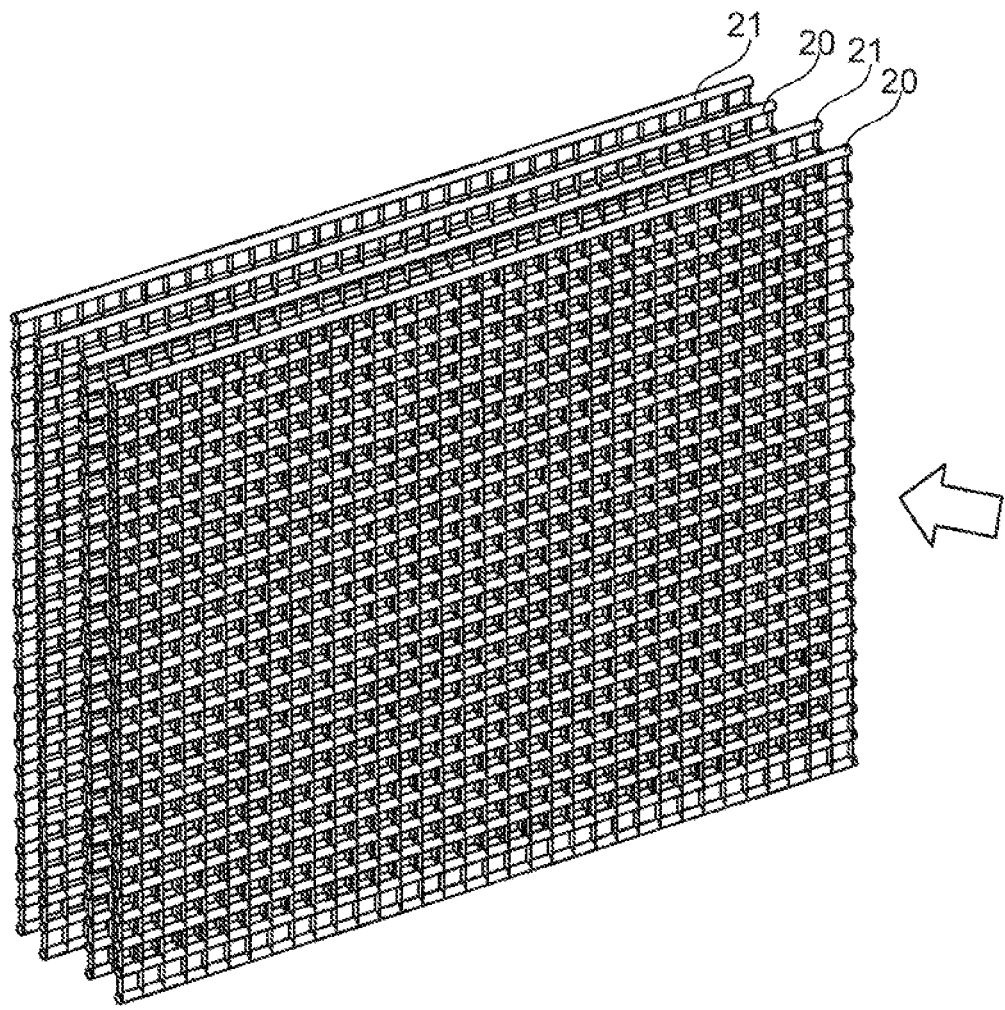
FIG. 6 shows a schematic perspective view of an embodiment variant of the odor filter of the filter unit according to the invention.

As shown in FIG. 6, the electrodes 20 and 21 are arranged alternately in relation to each other. The first and last electrode in the direction of flow can be either an air-permeable electrode 21 or an air-permeable high-voltage electrode 20.

Furthermore, the individual air-permeable counter electrode 21 shown in FIG. 5 can itself be composed of a plurality of air-permeable layers (n>=1). The same applies to the air-permeable high-voltage electrode 20.

Furthermore, the number of air-permeable electrodes 21 between two air-permeable high-voltage electrodes 20 can be greater than or equal to 1. The same applies in the opposite case likewise, i.e. the number of air-permeable high-voltage electrodes 20 between two air-permeable counter electrodes 21 is greater than or equal to 1.

Figure 11C:
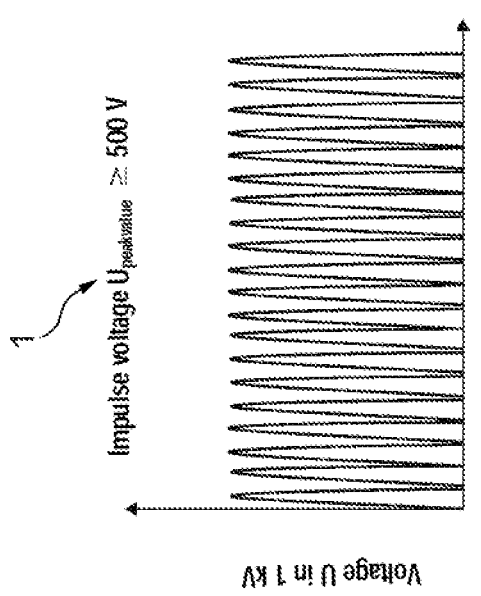

Concerning the voltage waveform, an impulse voltage with $U_{peakvalue}$>=500 V (see FIG. 11c) and a cycle duration T<=1 s is used for the air-permeable high-voltage electrode 20. The impulse voltage can be a positive or negative voltage type. Alternatively, a further possibility is an alternating voltage with $U_{effectivevalue}$>=500 V (see FIG. 11d) and a cycle duration T>=1 s. Various voltage waveforms are possible for the alternating voltage and the impulse voltage. For example, a sinusoidal, rectangular, triangular or sawtooth voltage waveform can be used. The air-permeable counter electrode is connected to the electrical counter potential, so that a changing electrical voltage difference $\Delta U$ can be guaranteed between the high-voltage electrode 20 and the counter electrode 21.

Alternatively, the air-permeable counter electrode 21 can be grounded. For this, the air-permeable counter electrode 21 is electrically connected to the protective conductor PE (protective earth).

Figure 13:
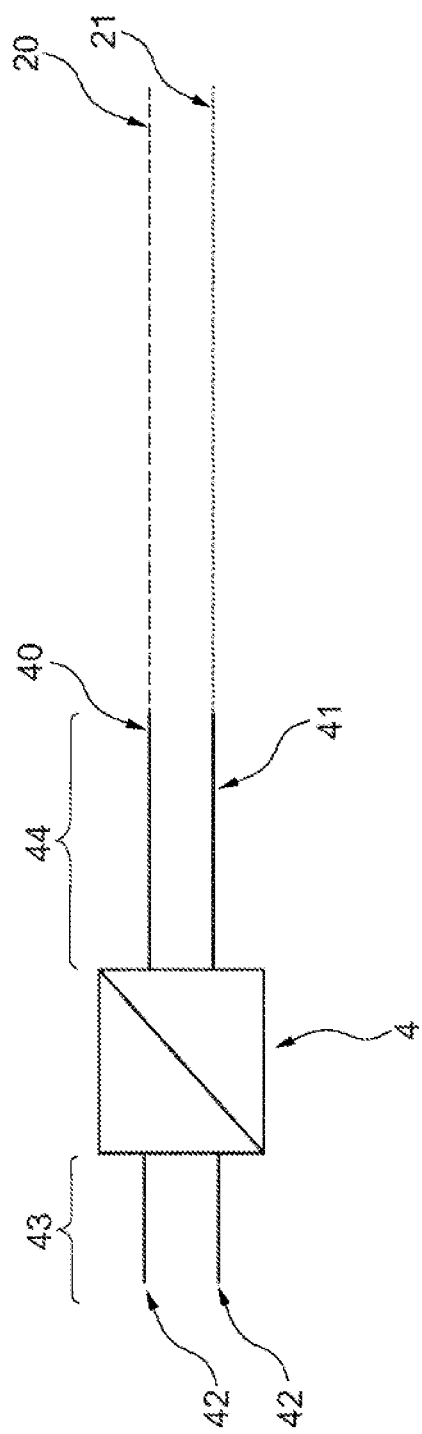
FIG. 13 shows a schematic block diagram of an embodiment variant of a high-voltage transformer.

The odor filter 2 can have a high-voltage transformer 4, which is shown schematically as a block diagram in FIG. 13. This high-voltage transformer 4 supplies the high-voltage electrode 20 and counter electrode 21 with electrical high voltage or electrical energy on the secondary side 44 via the power cables 40, 41. Possible voltage profiles on the secondary side 44 of the high-voltage transformer 4 are shown in the FIGS. 11c and 11d. On the primary side 43, the electrical power supply to the high-voltage transformer 4 is provided via the connection interface or power cables 42, e.g. using direct current or alternating current.

Concerning the relative arrangement/orientation of the individual air-conducting electrodes 20, 21, these are preferably so arranged as to be offset relative to each other as shown in the FIGS. 8 to 10 in order to ensure optimal ionization of the air which flows through and is laden with odor molecules, thereby in turn ensuring optimal neutralization of the odorous substances/odor molecules.

Figure 7:
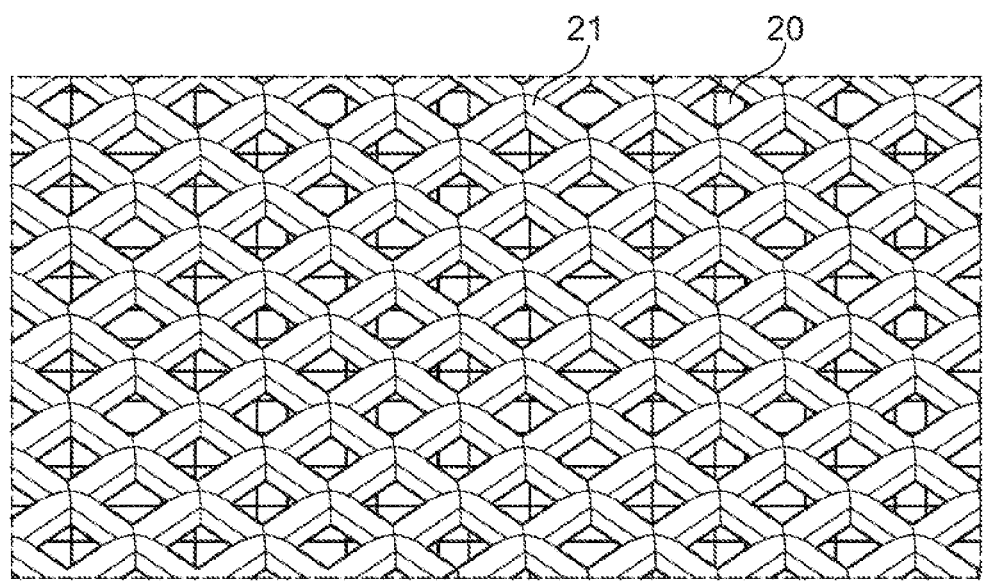
FIG. 7 shows a schematic detail view of a further embodiment variant of the odor filter of the filter unit according to the invention.

Furthermore, in the installed state the individual electrodes can be offset in the plane about an axis of rotation from 0 to 360° relative to each other. This is shown by way of example in FIG. 7, in which the electrodes 20, 21 are so positioned as to be offset i.e. rotated by 45° relative to each other.

According to the concept of the dielectrically impeded barrier discharge (DBD), an electrical displacement current I is produced between two electrodes with at least one dielectric when a temporally changing electrical voltage U, the so-called ionization voltage $U_{ionizationvoltage}$, is applied between these two electrodes under environmental conditions. The magnitude of the ionization voltage depends on many factors, e.g. the electrode geometry, the insulation material (dielectric), the gap width d, the voltage waveform, the gas composition, etc. Due to this ionization process in the ionization zone (plasma zone), reactive species are formed as a result of impact ionization processes, namely reactive oxygen species (ROS) and reactive nitrogen species (RNS). These reactive species are energetically highly reactive molecules which enter into chemical compounds with inter alia unpleasant odor molecules and other volatile organic compounds (VOCs), whereby these unpleasant odor molecules are chemically transformed into other chemical compounds. By means of chemical processes between the odor molecules and the reactive species, odors are consequently reduced or even eliminated completely. In accordance with this process/manner of functioning, air-permeable electrodes are used in the segment for odor neutralization within the inventive filter unit, resulting in ionization of the air between the electrodes in accordance with the principle of the dielectrically impeded barrier discharge. This ionization of the air in the ionization zone (plasma formation) results in the depletion/neutralization of olfactorily unpleasant odor molecules and other volatile chemical compounds (VOCs).

The present invention has a range of advantages.

The subject matter of the present invention is a compact autonomous ionizing filter unit which can eliminate both particles and olfactorily unpleasant odor molecules from the air.

By virtue of its design with the porous electrodes for reducing odors, the ionizing filter unit requires considerably less space than plasma filters which are currently available on the market.

The plasma filter (system for odor neutralization) that is used according to the invention consists solely of air-permeable electrodes which are arranged one behind the other and through which the air flows. By virtue of this simple invention for odor reduction, the plasma unit is cost-efficient with regard to the material and manufacturing costs.

The plasma unit (segment for odor neutralization) that is used according to the invention consists of porous or air-permeable electrodes which are arranged one behind the other and, in comparison with other plasma filters, has a far greater efficiency in respect of odor reduction. This is because a plasma wall is established by the porous electrodes during operation, and the air laden with odor molecules flows through said plasma wall. When the odor molecules in the air flow through this ionization zone or "plasma wall", these odor molecules undergo a complete chemical reaction with the reactive species. In other words, a complete intermixture of odor molecules and other reactive oxygen species (ROS) and reactive nitrogen species (RNS) occurs. Due to their geometric properties, the air-permeable electrodes of the plasma unit result in a better intermixture of the air flowing through.

As a result of the efficient intermixture of the air and consequently more efficient depletion of odor molecules and other VOCs, less electrical power (energy input) is required for the same filter efficiency in comparison with existing plasma systems.

The ionizing filter unit can be cleaned both in the dishwasher and by hand using detergent and water. The service life of such an ionizing filter unit is therefore unlimited. Both the air-permeable electrodes for odor reduction and the electrostatic filter can be rinsed of dirt and impurities. The existing plasma filters are not suitable for cleaning or even designed for this, depending on the manufacturer. This applies in particular to cleaning in the context of private domestic use.

The invention claimed is:

1. A filter unit for an air cleaning device, said filter unit comprising:
    an odor filter configured for odor neutralization and embodied as a device for plasma generation, said odor filter comprising an air-permeable high-voltage electrode and an air-permeable counter electrode arranged behind one another in a direction of flow of air, each of the air-permeable high-voltage electrode and the air-permeable counter electrode being formed by a panel element,
    wherein the counter electrode has a uniform pattern of openings that are air-permeable,
    the high-voltage electrode has a uniform pattern of openings that are air permeable, and
    the openings of the high-voltage electrode are offset from the openings of the counter electrode.

2. The filter unit of claim 1, further comprising an electrostatic filter which includes an ionization unit and a separation unit arranged downstream of the ionization unit in the direction of flow.

3. The filter unit of claim 2, wherein the separation unit of the electrostatic filter includes a live collecting electrode and a grounded collecting electrode, with the live collecting electrode and the grounded collecting electrode being air-impermeable plates or the live collecting electrode and the grounded collecting electrode being air-permeable electrodes.

4. The filter unit of claim 2, wherein the odor filter is arranged downstream of the electrostatic filter in the direction of flow.

5. The filter unit of claim 2, wherein the odor filter and the electrostatic filter are contained in a shared housing.

6. The filter unit of claim 1, wherein the air-permeable high-voltage electrode and the air-permeable counter electrode of the odor filter are arranged in an orientation which is inclined relative to the direction of flow.

7. The filter unit of claim 1, wherein at least one of the air-permeable high-voltage electrode and the air-permeable counter electrode of the odor filter has a surface on which an insulation coating is provided.

8. The filter unit of claim 1, wherein at least one of the high-voltage electrode and the counter electrode has a multilayered structure.

9. The filter unit of claim 1, wherein at least one of the high-voltage electrode and the counter electrode is made of an air-permeable material or an air-impermeable material with at least one air conduction opening.

10. The filter unit of claim 1, wherein at least one of the high-voltage electrode and the counter electrode is made of perforated plate, welded mesh, woven wire netting, expanded metal, sintered material and/or foamed material.

11. A filter unit for an air cleaning device, said filter unit comprising:
    an odor filter configured for odor neutralization and embodied as a device for plasma generation, said odor filter comprising an air-permeable high-voltage electrode and an air-permeable counter electrode arranged behind one another in a direction of flow of air, each of the air-permeable high-voltage electrode and the air-permeable counter electrode being formed by a panel element,
    wherein the high-voltage electrode and the counter electrode are arranged relative to each other in such a way that their structure is rotated about an axis in the plane of the respective one of the electrodes.

12. The filter unit of claim 1, wherein the odor filter includes a high-voltage transformer configured to generate a temporally changing high voltage for the high-voltage electrode of the odor filter.

13. An air cleaning device, comprising a filter unit, said filter unit comprising:
    an odor filter configured for odor neutralization and embodied as a device for plasma generation, said odor filter comprising an air-permeable high-voltage electrode and an air-permeable counter electrode arranged behind one another in a direction of flow of air, each of the air-permeable high-voltage electrode and the air-permeable counter electrode being formed by a panel element,
    wherein the counter electrode has a uniform pattern of openings that are air-permeable,
    the high-voltage electrode has a uniform pattern of openings that are air permeable, and
    the openings of the high-voltage electrode are offset from the openings of the counter electrode.

14. The air cleaning device of claim 13, wherein the air cleaning device is a vapor extraction device, said filter unit being arranged upstream of a fan of the vapor extraction device.

15. The air cleaning device of claim 13, wherein the air-permeable high-voltage electrode and the air-permeable counter electrode of the odor filter are arranged in an orientation which is inclined relative to the direction of flow.

16. The air cleaning device of claim 13, wherein at least one of the air-permeable high-voltage electrode and the air-permeable counter electrode of the odor filter has a surface on which an insulation coating is provided.

17. The air cleaning device of claim 13, wherein at least one of the high-voltage electrode and the counter electrode has a multilayered structure.

18. The air cleaning device of claim 13, wherein at least one of the high-voltage electrode and the counter electrode is made of an air-permeable material or an air-impermeable material with at least one air conduction opening.

19. The air cleaning device of claim 13, wherein at least one of the high-voltage electrode and the counter electrode is made of perforated plate, welded mesh, woven wire netting, expanded metal, sintered material and/or foamed material.

20. The air cleaning device of claim 13, wherein the high-voltage electrode and the counter electrode are arranged relative to each other in such a way that their structure is rotated about an axis in the plane of the respective one of the electrodes.

* * * * *